United States Patent [19]
Ryan, Jr.

[11] Patent Number: 5,681,264
[45] Date of Patent: Oct. 28, 1997

[54] SHIELDED ILLUMINATION DEVICE FOR OPHTHALMIC SURGERY AND THE LIKE

[76] Inventor: Edwin H. Ryan, Jr., 752 Goodrich Ave., St. Paul, Minn. 55105

[21] Appl. No.: 547,930

[22] Filed: Oct. 25, 1995

[51] Int. Cl.$^6$ .................................................. A61B 1/06
[52] U.S. Cl. ..................... 600/177; 600/160; 600/171; 600/161; 600/249; 606/4; 606/17; 362/32; 362/344; 362/347
[58] Field of Search ...................... 600/160, 170, 600/171, 176, 177, 181, 182, 183, 247, 248, 249; 606/1, 4, 5, 6, 13, 16, 17, 161, 166; 362/32, 109, 332, 335, 338, 119, 341, 344, 347

[56] References Cited

U.S. PATENT DOCUMENTS

| | | | |
|---|---|---|---|
| 4,566,438 | 1/1986 | Liese et al. | 600/182 X |
| 5,335,648 | 8/1994 | Kozawa et al. | 128/6 |
| 5,351,168 | 9/1994 | Easley | 362/32 |
| 5,352,221 | 10/1994 | Fumich | 606/15 |
| 5,431,646 | 7/1995 | Vassiliadis et al. | 606/6 |

*Primary Examiner*—Beverly M. Flanagan
*Attorney, Agent, or Firm*—Polster, Lieder, Woodruff & Lucchesi

[57] ABSTRACT

A surgical illumination probe includes an optical fiber with a proximal end and a distal end, a connector disposed at the proximal end of the optical fiber (the connector being adapted for connection to a source of illumination and for holding the proximal end of the optical fiber in position to accept light from the illumination source), and a handpiece disposed generally at the distal end of the optical fiber. The handpiece has a handpiece body and a needle extending distally from the handpiece body, with the optical fiber extending generally through the handpiece and extending slightly past the distal end of the needle. The handpiece is of a size suitable for one-handed operation by a human user, and the needle is of a size suitable for insertion into a human eye. The probe also includes structure at the distal end of the optical fiber for dispersing light passing from the illumination source through the cable to broaden the area on which the light impinges, and a shield disposed proximally of at least a portion of the dispersing means to prevent light from impinging upon a predetermined area. The predetermined shielded area is disposed proximal the needle and spaced transversely therefrom.

17 Claims, 1 Drawing Sheet

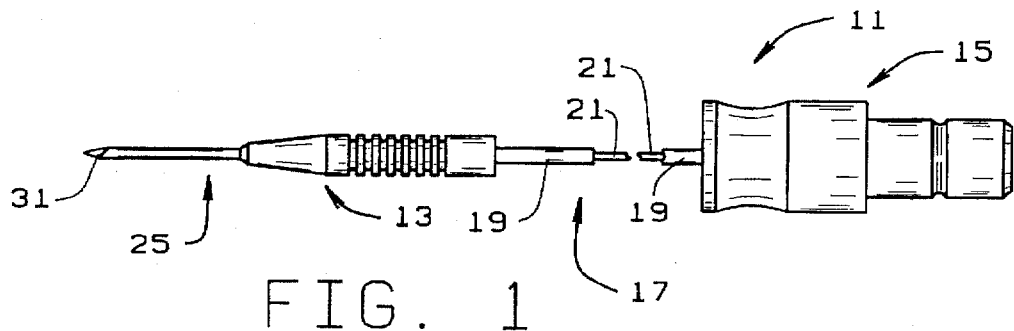
FIG. 1
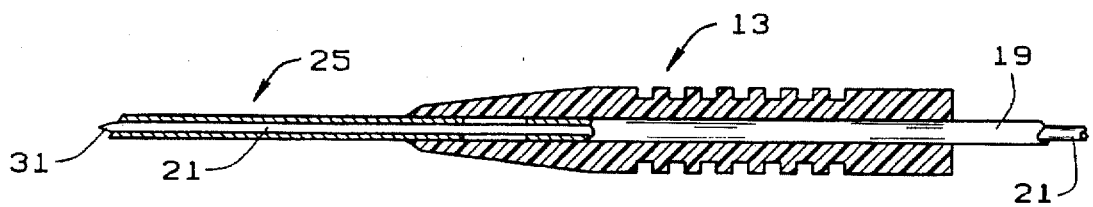
FIG. 2
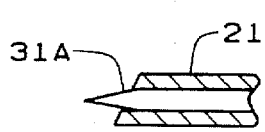
FIG. 2A
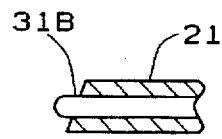
FIG. 2B
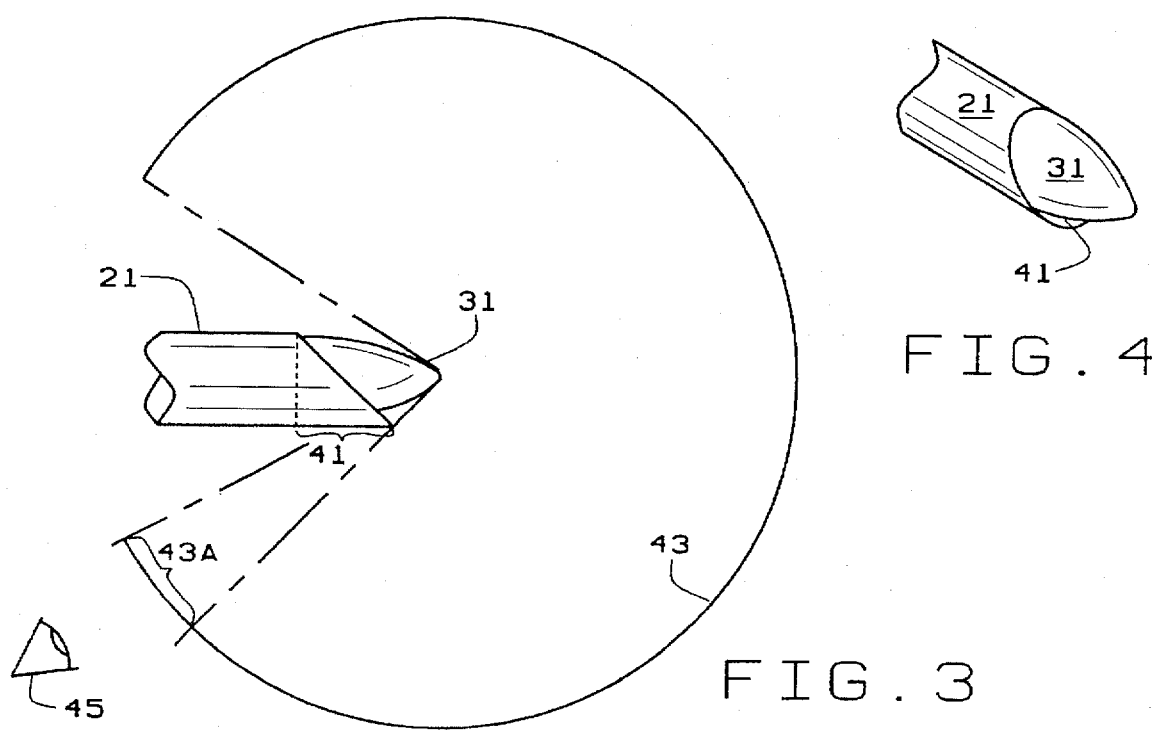
FIG. 4
FIG. 3

SHIELDED ILLUMINATION DEVICE FOR OPHTHALMIC SURGERY AND THE LIKE

BACKGROUND OF THE INVENTION

This invention relates to surgery and more particularly relates to illumination devices particularly suited for ophthalmic surgery and the like.

It is known that ophthalmic surgery (and other types of surgery such as laparoscopic and arthroscopic surgery) as well as various procedures such as endoscopy typically require an illumination probe or device which provides illumination for the area under treatment. To provide the best possible visualization for the physician/user of the device, it is preferred that the output of the illumination device be broadband (simulating sunlight to some degree), that the device itself be rather small (so as to not interfere with other instruments being used in the procedure, for example), that the device illuminate a relatively large area at one time, that the light output over the illuminated area be fairly uniform (eliminating dark spots, excessively bright spots, etc.) and not project back towards the operator so as to cause glare that interferes with viewing.

Often the illumination is transmitted from an illumination source (disposed at some distance from the patient) through an optical fiber cable to a handpiece which is manipulated by the physician/user or an assistant to provide illuminating light on the desired area. Optical fiber cables do a good job of providing broad spectrum light from a suitable illumination source, but the light output of optical fibers could be improved. For example, the numerical aperture of optical fibers are typically rather small, with the result that the field of illumination for these devices is smaller than could be desired. Moreover, these devices are most often used in liquids (saline solutions and the like) which further reduces the field of illumination. A narrow field of illumination is adequate for conventional ophthalmic surgical viewing systems, but recently viewing systems have been developed which give the surgeon a more panoramic view of the eye, and require greater dispersion of light to illuminate this larger area. To more uniformly disperse the illumination, lenses have been used as the end of the optical fiber to spread the light. Moreover, at least one device (manufactured by Trek Medical) has been proposed to spread the light by changing the distal configuration of the optical fiber itself from the standard blunt shape to a cone shape. Infinitech, Inc., licensee of the present invention, has also developed a distal configuration of the optical fiber (shown in U.S. Pat. No. 5,351,168) which is believed to address the problem of dispersing the light in a superior manner.

All these devices could be improved however. For example, it has been found that the wide angle illumination devices such as those described above result in light from the illumination probe being transmitted directly into the surgeon's eyes. This, of course, is undesirable and somewhat defeats the purpose of having a wide angle illumination device. This problem makes fine structures adjacent to the probe (e.g. vitreous fibers) quite difficult to see. In addition, glare from the probe becomes increasingly problematic in a gas-filled eye or with poor media. What would be preferred in some instances is a wide angle illumination device which provides means for protecting the surgeon's eyes from direct illumination so as to not affect the surgeon's view of the surgical area.

SUMMARY OF THE INVENTION

Among the several objects and features of the present invention may be noted the provision of an improved illumination device which is especially suited for ophthalmic, laparoscopic, or arthroscopic surgery and endoscopy and the like.

Another object is the provision of such an illumination device which provides an improved field of illumination while at the same time allowing the surgeon's eyes to be protected from direct illumination.

A third object is the provision of such an illumination device which is readily controllable by the surgeon.

A fourth object is the provision of such an illumination device which is reliable, yet relatively simple to manufacture.

Other objects and features will be in part apparent and in part pointed out hereinafter.

Briefly, an illumination probe for ophthalmic surgery and the like includes an optical fiber having a proximal end and a distal end and a connector disposed at the proximal end of the optical fiber. The connector is adapted for connection to a source of illumination and for holding the proximal end of the optical fiber in position to accept light from the illumination source. A handpiece is disposed generally at the distal end of the optical fiber and has a handpiece body and a needle extending distally from the handpiece body. The optical fiber extends generally through the handpiece. It is preferred that the handpiece be of a size suitable for one-handed operation by a human user, and that the needle be of a size suitable for insertion into a cavity in the human body such as the interior of a human eye. A lens or similar structure is disposed at the distal end of the optical fiber for dispersing light passing from the illumination source through the cable to broaden the area on which the light impinges. A shield is provided proximally of at least a portion of the dispersing means to prevent light from impinging upon a predetermined area, which predetermined area is disposed proximal the needle and spaced transversely therefrom.

BRIEF DESCRIPTION OF THE DRAWINGS

FIG. 1 is a side elevation of the illumination device of the present invention;

FIG. 2 is an enlarged sectional view of distal end of the device of FIG. 1;

FIGS. 2A and 2B are partial sections similar to a portion of FIG. 2, illustrating other possible construction of a light dispersing element used in the present invention;

FIG. 3 is an enlarged elevation illustrating use of the illumination device of the present invention; and FIG. 4 is a perspective view similar to FIG. 3, showing the distal end of the illumination device of FIG. 1.

Similar reference characters indicate similar parts throughout the several views of the drawings.

DESCRIPTION OF THE PREFERRED EMBODIMENT

Turning to the drawings, an illumination device 11 of the present invention includes a handpiece 13, an illumination light source connector 15, and an optical fiber cable 17. Optical fiber cable 17 typically includes a protective sheath 19 covering either a single or multiple optical fibers 21. A single plastic fiber is preferred, although multiple fibers or glass fibers could also be used in the present invention.

A hollow metal probe needle 25 is connected to the body of handpiece 13 and extends distally therefrom. The body of handpiece 13 is used to manipulate the position of probe needle 25 to provide illumination passing through the needle to the desired locations during an operation or procedure. For ophthalmic surgery, probe needle 25 is of a size suitable for insertion into a human eye. Illumination devices for other operations and procedures could differ in size. Although illumination device 11 is described herein solely as providing illumination, it should be understood that various other features could be added thereto. For example, a pie, an irrigation/aspiration lumen, a laser capability, and various other features could be added as desired.

As can be readily seen in FIG. 1, optical fiber cable 17 terminates proximally in illumination connector 15 in such a manner that it is exposed to illuminating light from the light source. The optical cable extends for any desired length (such an six feet or so) and terminates distally adjacent probe needle 25. Optical fiber cable 17 thereby forms an optical path for the illuminating light from the light source to an eye (or other body part or organ).

As can be seen more clearly in FIG. 2, sheath 19 terminates in the body of handpiece 13 while the optical fiber 21 itself terminates at the distal end of the probe in a bullet-shaped tip 31. Such a tip is only one of the possible dispersing devices usable in the present invention. Other alternatives are the cone-shaped tip 31A shown in FIG. 2A, and the hemispherical tip 31B shown in FIG. 2B. Any suitable lens configuration could be used as well. Although tip 31 is preferably formed on the distal end of optical fiber 21, it may also be formed as a separate part which is suitably secured to the distal end of probe needle 25. Tip 31 is preferably shaped so as to provide illumination over as wide a field of illumination as possible when the tip is disposed in a location for use. Although the present invention can be used with a wide variety of light dispersing structures, such as those described above, it is described hereinafter in connection with the bullet-shaped tip of FIG. 2.

As can be seen in FIGS. 3 and 4, the present invention includes a shield 41 disposed at the end of needle 21, and preferably parallel thereto. Preferably the shield is an extension of needle 21 and is formed integrally with the needle as a single piece. This may be accomplished, for example, by suitably beveling the distal end of needle 21 to provide the wedge shaped shield 41. A bevel angle of approximately 45 degrees has been found to be satisfactory. This shield is relatively pointed at its distal end and widens proximally (as best seen in FIG. 4) in a smooth manner. It is preferred that any transitions in shield 41 be smooth to reduce the possibility of unnecessary trauma to the patient.

It is preferred that the tip of the dispersing structure, in this case the bullet tip of the optical fiber, extend distally past the distal end of the shield a predetermined distance such as 0.005" to 0.020". This allows illumination from the optical fiber to illuminate the vast majority of the operative field (indicated by the line 43 in FIG. 3) while shielding the eye 45 of the surgeon from direct illumination. In other words, shield 41 blocks direct illumination from the area 43A. By suitable manipulation of handpiece 13 the user can always insure that the shielded area includes the user's eye(s). This invention affords multiple significant functional benefits. The shielding eliminates glare in all viewing situations, which is particularly .important and beneficial when the media are poor. Also, the absence of glare allows the surgeon to visualize fine structures (such as the vitreous) adjacent to the probe, something this is not possible with present diffuse illumination probes. This property allows the shielded probe to be more versatile in that it can be effectively used with both conventional and panoramic viewing systems, something not possible with current illumination devices. A surgeon could use the shielded illumination probe as the only probe during a surgery, rather than using different probes for conventional and panoramic viewing, as is now done.

It should be appreciated that the shielded area 43A not only has the increasing width shown in FIG. 3 the farther from the tip one measures, but it also has an increasing breadth as well. That is, the shield of FIGS. 3 and 4 preferably covers less and less of the optical fiber as one moves distally so as to limit the illumination of the operative field as little as necessary. This feature makes it fairly easy to protect the surgeon's eye from direct illumination while at the same time adequately illuminating the operative field. It also insures that light from the opposite side of the dispersing structure (measured circumferentially) is not blocked at all. In other words, the shield blocks light from entering the surgeon's eye, but allows the surgeon to see past the distal tip since the apparent cross-section is less than that of the distal end of the needle itself. If desired, the shield can be formed to have an apparent cross-section greater than that of the dispersing means itself, depending upon the application.

Although shield 41 is preferably an extension of needle 21, the shield can be formed in other ways. For example, shield 41 may be painted directly onto the relevant portion of dispersing element 31. In addition, although shield 41 is described above as performing only a shielding function, it should be understood that by suitably shaping shield 41 it may perform additional functions if desired, such as a pic or a knife blade.

What is claimed is:

1. An illumination probe for ophthalmic surgery comprising:

an optical fiber having a proximal end and a distal end;

a connector disposed at the proximal end of the optical fiber, said connector being adapted for connection to a source of illumination and for holding the proximal end of the optical fiber in position to accept light from the illumination source;

a handpiece disposed generally at the distal end of the optical fiber, said handpiece having a handpiece body and a needle extending distally from the handpiece body, said optical fiber extending generally through the handpiece, said handpiece being of a size suitable for one-handed operation by a human user, and the needle being of a size suitable for insertion into a cavity in the human body such as the interior of a human eye;

means at the distal end of the optical fiber for dispersing light passing from the illumination source through the cable to broaden the area on which the light impinges;

a shield disposed proximally of at least a portion of the dispersing means to prevent light from impinging upon a predetermined area, said predetermined area being disposed proximal the needle and spaced transversely therefrom, the distal end of the shield being disposed proximally of the distal end of the optical fiber.

2. The ophthalmic surgery illumination probe as set forth in claim 1 wherein the shield is integrally formed with the distal end of .the needle.

3. The ophthalmic surgery illumination probe as set forth in claim 1 wherein the shield extends distally to form a predetermined area which is generally wedge-shaped.

4. The ophthalmic surgery illumination probe as set forth in claim 1 wherein the shield is pointed distally and widens proximally.

5. The ophthalmic surgery illumination probe as set forth in claim 4 wherein the width of the shield varies smoothly from distal to proximal end.

6. The ophthalmic surgery illumination probe as set forth in claim 1 wherein the shield circumference covers less of the dispersing means as the distal end of the shield is approached.

7. The ophthalmic surgery illumination probe as set forth in claim 1 wherein the distal end of the shield is spaced approximately 0.005" proximally from the distal end of the optical fiber.

8. The ophthalmic surgery illumination probe as set forth in claim 1 wherein the shield is disposed generally parallel to the needle.

9. The ophthalmic surgery illumination probe as set forth in claim 8 wherein the distalmost portion of the shield is spaced from the longitudinal axis of the optical fiber generally the same distance as the needle is spaced from the longitudinal axis of the optical fiber.

10. The ophthalmic surgery illumination probe as set forth in claim 1 wherein the shield is a one-piece extension of the needle.

11. The ophthalmic surgery illumination probe as set forth in claim 10 wherein the shield is a beveled extension of the needle.

12. The ophthalmic surgery illumination probe as set forth in claim 11 wherein the bevel angle of the beveled extension is approximately 45°.

13. The ophthalmic surgery illumination probe as set forth in claim 1 wherein the dispersing means disperses light generally uniformly as measured circumferentially around the dispersing means, and wherein said shield is disposed to block light from only a circumferential portion of the dispersing means.

14. The ophthalmic surgery illumination probe as set forth in claim 1 wherein the dispersing means extends longitudinally from the distal end of the needle, said shield covering a portion of the dispersing means distally from the distal end of the needle, said shield terminating short of the distal end of the dispersing means.

15. The ophthalmic surgery illumination probe as set forth in claim 1 wherein the shield is disposed to block light from entering a surgeon's eye yet has an apparent cross-section less than the distal end of the needle, whereby the surgeon may see past the distal tip during use.

16. The ophthalmic surgery illumination probe as set forth in claim 1 wherein the shield is formed of a material painted onto a predetermined portion of the dispersing means.

17. The ophthalmic surgery illumination probe as set forth in claim 1 wherein the shield is spaced from the dispersing means and is disposed to be used as an implement such as a pic or a knife blade.

* * * * *